(12) United States Patent
Bernstein et al.

(10) Patent No.: US 6,256,373 B1
(45) Date of Patent: Jul. 3, 2001

(54) X-RAY FLUORESCENCE INSTRUMENT

(76) Inventors: Karl Bernstein, 432 Shenandoah, Thousand Oaks, CA (US) 91360; Charles C. Kidd, 17334 Trosa St., Grenada Hills, CA (US) 91344

( * ) Notice: Subject to any disclaimer, the term of this patent is extended or adjusted under 35 U.S.C. 154(b) by 0 days.

(21) Appl. No.: 09/374,929

(22) Filed: Aug. 16, 1999

Related U.S. Application Data

(60) Provisional application No. 60/097,042, filed on Aug. 19, 1998.

(51) Int. Cl.[7] ............................................. G01N 23/223
(52) U.S. Cl. .............................. 378/45; 378/44; 702/23; 250/389
(58) Field of Search ................................. 378/45, 44, 6, 378/70; 250/380; 702/23

(56) References Cited

U.S. PATENT DOCUMENTS

| | | | |
|---|---|---|---|
| 3,916,200 | * 10/1975 | Sparks, Jr. et al. | 250/389 |
| 3,920,999 | * 11/1975 | Drexler et al. | 378/119 |
| 4,510,573 | * 4/1985 | Boyce et al. | 702/23 |
| 5,369,578 | * 11/1994 | Roscoe et al. | 702/8 |

* cited by examiner

Primary Examiner—Robert H. Kim
Assistant Examiner—Pamela R. Hobden
(74) Attorney, Agent, or Firm—Fulbright & Jaworski L.L.P.

(57) ABSTRACT

An x-ray fluorescence instrument for measuring the presence of lead in a sample. The lead is bombarded with gamma rays from a source thereof and in turn, emit x-rays. The x-rays are detected by a scintillation detector which emits photons that are directed to a photomultiplier tube which provides signals to an electronic processor including multi-channel analyzers to provide output signals representative of the lead present in the sample. The instrument includes a cone plug disposed between the gamma ray source and the detector to prevent gamma rays from directly striking the detector.

11 Claims, 1 Drawing Sheet

X-RAY FLUORESCENCE INSTRUMENT

This Application is based upon Provisional Application No. 60/097,042 filed Aug. 19, 1998 for Nuclear/X-Ray Fluorescence Determination of Lead and Other Elements by Karl Bernstein and Charles Chapman Kidd.

BACKGROUND OF THE INVENTION

It has become apparent in recent years that the incidence of lead in the atmosphere, the soil and other surrounding environmental areas occupied by human beings is greater than previously anticipated. It is now recognized that lead can be airborne and may contaminate areas in which workers are housed while performing their day-to-day employment tasks. It has also become recognized that as a result of the use prior to the 1978 of paint containing lead, substantial soil contamination around older school buildings and older houses has resulted. In addition, upon the demolition of older buildings which were painted with lead containing paint, particles of lead may become airborne thus creating a toxic environment for the demolition workers and other individuals within the general demolition area.

There are many industries and activities in which lead in one form or another is commonly used. For example, in shooting galleries where live ammunition is utilized lead projectiles are propelled from the weapons toward the targets. The propelling of the lead projectiles and their impact with the target and with the projectile restraining walls beyond the targets creates a situation in which particles of lead enter the ambient atmosphere and remain airborne for a substantial period of time.

It is also known that in many industries where radiation of one form or another occurs, lead has been used as a common material for shields to protect personnel from bombardment by nuclear radiation. The presence of such lead shields in any significant amount generates a situation where lead particles can contaminate the ambient atmosphere. A similar type of situation occurs in industries in which lead is an integral or component part of the activity or the resulting product. Typical examples of such instances are where soldering occurs such as in the manufacture of electronic devices, the mining of lead, the smelting of ores containing lead, the manufacture of batteries which contain lead therein, the refining of petroleum products and many other industries which those skilled in the art will recognize.

As a result of the extensive lead contamination of the ambient atmosphere, it becomes extremely desirable to monitor the lead content of the atmosphere to determine whether or not personnel present may be subjected to a sufficient amount of lead to constitute a toxic danger.

Typically monitoring the ambient under such circumstances is accomplished by passing the ambient air, or a portion thereof, through an appropriate filter having sufficiently small pores to capture the airborne lead particles or at least a substantial number thereof. The filter containing the lead particles can then be subjected to appropriate measurement to determine the lead content in the ambient atmosphere to determine whether or not sufficient lead particles exist to constitute a potential danger to personnel in that area. This measuring process can be accomplished on a periodic basis which is determined by the surrounding circumstances and the application involved. For example the measuring can be done on a daily basis with appropriate records kept to track changes in the airborne lead content of the ambient atmosphere on a day-to-day basis. Under certain circumstances, the activity involved may be such that the measuring should be conducted on an hour-by-hour type basis or even more frequently in order to detect the existence of an immediate problem which may have occurred as a result of a malfunction of manufacturing processes or equipment thus constituting a sufficient danger that the immediate area should be cleared of all personnel for a time sufficient to recirculate the ambient atmosphere and remove the excess airborne lead particles therefrom.

To accomplish the measurement of the lead particles which may be present either in the air, the soil or other portions of the environment, it is recognized that x-ray fluorescence (xrf) is a very useful elemental analysis technique. Xrf uses common nuclear instrumentation to provide extra-nuclear indications of elemental composition both qualitatively and quantitatively. Xrf works best with medium high to high atomic number elements which includes lead.

The method usually uses gamma ray bombardment of the lead particles to excite x-ray emission from them and then uses scintillation or semiconductor detectors and computer-based multi-channel analyzers (MCA) to complete the elemental analysis. Small isotopic sources of gamma rays generally are preferred to x-ray sources of excitation.

One of the problems associated with xrf utilizing gamma ray excitation is that comparatively few of the gamma rays will be observed by traces of lead in the field of view of the xrf instrument head. A substantially larger fraction of the gamma rays emitted by the excitation source will be scattered and ultimately detected by the MCA as lower energy gamma rays.

The scatter gamma rays create a background noise and as a result will interfere with the desired x-ray signal. This results because gamma rays and x-rays are substantially the same in all ways except for their motive creation and the x-rays of value and the scattered gamma rays are combined in their distribution throughout the spectrum. Their combined presence in the spectrum presents data processing and/or instrument hardware requirements. One resolution of the difficulty of this combined scattered gamma ray and desired x-ray information is to use semi-conductor detectors which greatly reduce the interference relative to that of scintillation detectors. However, to use the semi-conductor detectors substantially increases the cost of the instrument. As a result, scintillation detection systems are highly desirable in an instrument of the type with which the present invention is concerned.

It is thus desirable that an instrument utilizing a scintillation detection system in which appropriate controls are effected to substantially mitigate the interference of scattered gamma rays emitted by the excitation source with the x-ray signals received from the excited particles of lead which are to be detected is used. Without effective control the gamma rays will enter the ambient in all directions from the isotopic source and even if some containment mechanism is utilized, these gamma rays will reflect one or more times and still interfere with the operation of the instrument by providing improper activation of the scintillation detector.

SUMMARY OF THE INVENTION

An x-ray fluorescence instrument for detecting radiation emanating from a sample to be measured which instrument includes a detector, means for positioning a sample adjacent the detector means, a source of radiation contained within a mounting head which includes a shield substantially surrounding said radiation source and defining an opening therethrough for passage of radiation from the source toward the sample. The opening is defined by a conical surface diametrically diverging away from the opening. The instrument further comprises a plug disposed between the shield opening and the sample to preclude radiation from the source directly striking the detector.

BRIEF DESCRIPTION OF THE DRAWING

The single FIGURE represents a schematic diagram of an x-ray fluorescence instrument constructed in accordance with the principles of the present invention.

DETAILED DESCRIPTION

Figure 1:
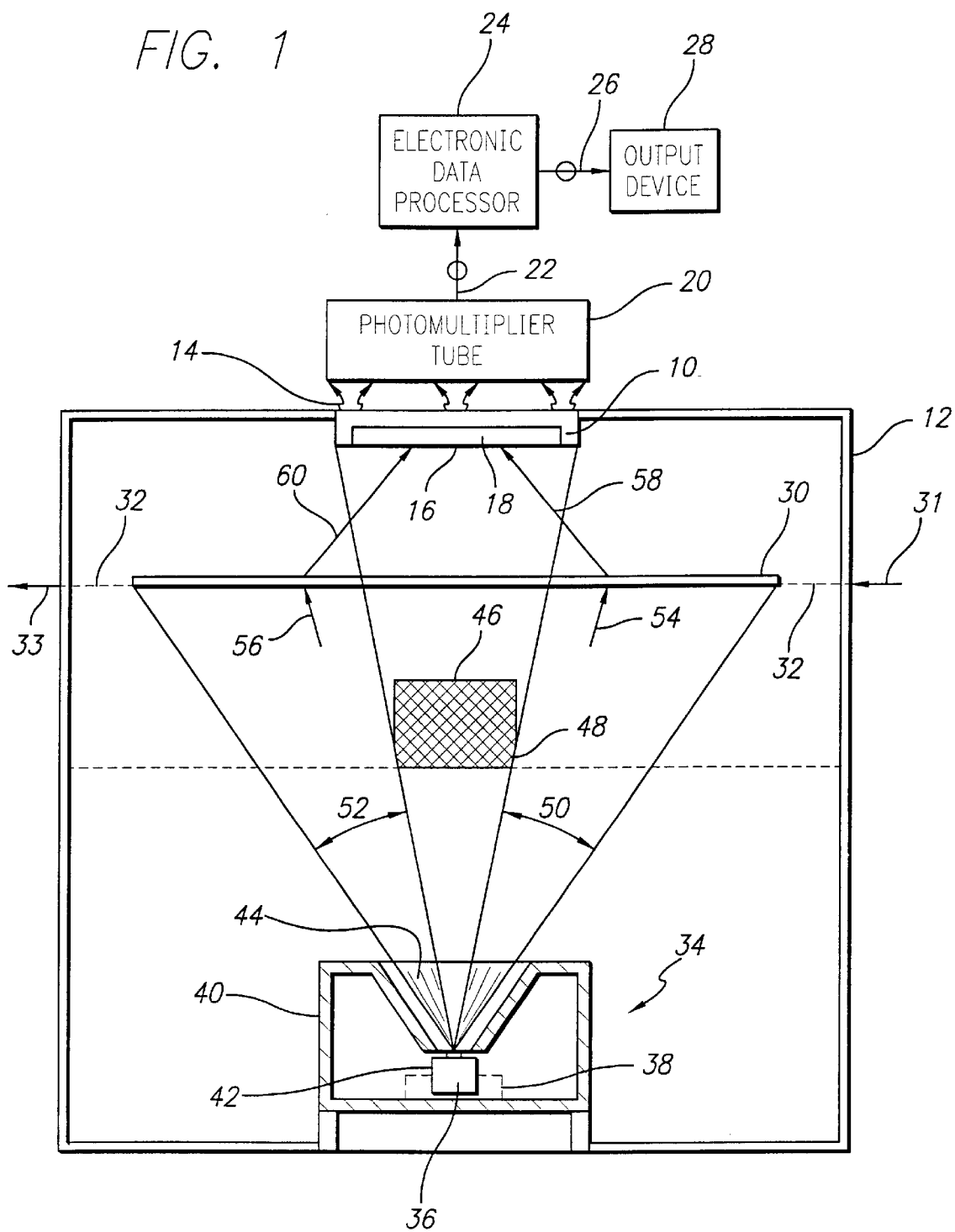

Referring now to the drawing, there is illustrated an x-ray fluorescence instrument constructed in accordance with the principles of the present invention. As is therein shown, a scintillation detector 10 such as a sodium iodide crystal is mounted to a housing 12 constructed of material which functions as a shield or gamma and x-rays. The scintillation detector 10 emanates photons 14 therefrom in response to x-ray radiation striking the surface 16 and passing through the window 18. The photons 14 strike the surface of a photomultiplier tube 20 which generates a signal in response thereto as is well known in the art. The signal is transmitted through an appropriate cable 22 to an electronic data processor 24 which will include multi-channel analyzers adapted to process the signals received from the photomultiplier tube 20. The output signals from the electronic data processor 24 are then passed to an output device 28 by the appropriate cabling 26 all as well known to those skilled in the art.

Positioned internally of the housing 12 is a sample 30 which is supported by appropriate means as shown by the dashed lines 32. The sample 30 will contain the materials which are to be analyzed by the x-ray Fluorescence instrument of the present invention. As above discussed, the sample 30 will typically be a filter through which ambient air has been passed so as to trap the airborne particles of lead. The filter 30 will be removed from the filtering apparatus on the desired periodic basis and inserted into the housing 12 of the x-ray Fluorescence instrument.

Although the specific example of a filter is used it should be recognized that other apparatus may be employed. For example, if continuous monitoring is to be accomplished the sample 30 may be a baffle device through which ambient air is continuously passed as shown by inlet arrow 31 and the outlet arrow 33. A simple fan or compressor may be operated to create a sufficient pressure to flow ambient air in a controlled amount through a baffle having a predetermined configuration to provide a desired volume of ambient air for measurement of airborne lead particles contained therein. A typical flow rate for such purposes would be on the order of 1 to 3 cubic feet per minute. The baffle would be designed to assure that any single lead particle would not generate an undue number of x-ray signals as it passes through the instrument.

Also positioned within the housing 12 is a head 34 which is adapted to receive a source 36 of gamma rays. Typically, the source 36 will be a relatively small isotopic source of such gamma rays and for example, may be Cobalt-57. The source 36 is mounted within an appropriate holder 38 which in turn is positioned internally of a shield 40. The shield 40 is preferably constructed of a non-radioactive high atomic number material which will effectively trap the gamma rays not allowed to directly pass from the head 34 or at least require them to negotiate multi-scattering around the inner surfaces of the shield 40. Preferably the shield 40 is constructed of tungsten material.

An important feature of the present invention is that the tungsten shield 40 defines an opening 42 adjacent the source 36 through which gamma rays may pass. The opening is further defined by an outwardly diverging conical surface 44 along which the gamma rays are directed toward the sample 30. As above referred to the gamma rays will leave the source 36 in all directions and in substantially straight lines. By providing the tungsten shield 40, only those gamma rays exiting the source 36 through the opening 42 will be directed toward the sample 30. The remainder of the gamma rays which would otherwise be scattered throughout the internal portion of the housing 12 and would interfere with the signal being generated by the detector 10 are effectively trapped within the shield 40 and absorbed by the tungsten. Through utilization of the outwardly diverging conical surface 44, the gamma rays are directed upwardly as viewed in the figure and toward the sample 30.

It should also be recognized by the those skilled in the art that it is not desirable for gamma rays to directly impact the surface of the detector 10. Therefore, there is positioned a plug 46 between the opening 42 and the detector 10. The plug 46 is constructed in such a manner that the exterior surface 48 is also conically shaped to allow the passage of gamma rays thereby but to such a degree that any gamma rays passing thereby if they were to continue in a straight line toward the detector 10 would just miss the detector. That is the plug 46 effectively shields the detector 10 from radiation emanating directly from the source so that it cannot directly strike the detector 10. The plug 46 must have a density such that it can shield the source gamma rays insofar as the detector 10 is concerned. It is also desirable that the atomic number of the material from which the plug 46 is made be different by a significant amount from that of the material which is contained in the sample 30 and is to be measured. The further the separation, the less likely the x-ray energy generated by the plug 46 will interfere with the signal which it is desired to detect with the detector 10. The diameter of the plug 46 must be such that it will effectively shadow or shield the detector from the gamma rays. The thickness of the plug 46 must be such that it is sufficient to be able to stop the gamma rays; that is gamma rays will not penetrate the plug 46 and travel directly onto the detector 10. Obviously, the thickness of the cone plug 46 will depend upon the source of the gamma rays. If the source is, as above suggested, Cobalt 57 then the thickness of plug 47 should be one to two centimeters. In a preferred embodiment of the present invention, the plug 46 is constructed of tungsten material.

With the construction of the shield and the plug as above described, a conical beam of gamma rays having the center thereof removed, as shown by the arrows 50–52, will emanate from the source 36 and strike the sample 30, that is, an annulus of gamma rays will impinge upon the sample 30. As the gamma rays strike the sample 30, as illustrated at 54 and 56, the particles of lead trapped within the sample 30 have the energy content thereof increased by absorption of the gamma rays 54–56. The release of this absorbed energy then results in the lead particles radiating x-rays as shown at 58 and 60. These x-rays then will strike the detector 10 by passing through the window 18 causing the photons 14 to be radiated therefrom. Obviously, there will be a great deal more radiation activity than is illustrated in the figure and the x-rays emanating from the sample will radiate in directions other than directly at the detector 10. However, for simplicity of illustration and discussion, only the two gamma rays 54–56 resulting in the radiation of the x-rays 58 and 60 have been illustrated and described.

As above indicate, the photons will be processed by the multi channel analyzers in the electronic data processor 24 and provide a signal to the output device 28 which is representative of the elements in the sample. For example, lead will provide a peak at approximately 75 Kev and 73 Kev with other elements at different positions on the spectrum. The MCA will be programmed to separate the signals representative of the desired element being monitored, such as lead.

As above indicated and as known to those skilled in the art, there will be gamma rays as well as x-rays within the instrument which are not absorbed by cone plug 46, the sample 30, nor by the detector 10. The housing 12 will be constructed of a material which will either absorb or deflect the gamma rays and the x-rays which strike the interior surface thereof. As a result personnel resident in the general area in which the instrument is being used will be protected from the resultant gamma rays and x-rays.

There has thus been described a simple x-ray fluorescence instrument for detecting radiation emanating from a sample containing material which is to be measured and which utilizes gamma rays as a source of radiation to generate the x-rays to be detected. The structure of the present invention concentrates or focuses the gamma rays so that they impinge upon the sample and do not directly impinge upon the detector while at the same time controlling the emanation of the gamma rays from the source.

What is claimed is:

1. An x-ray fluorescence instrument for detecting radiation emanating from a sample to be measured comprising:
    means for detecting radiation;
    means for positioning a sample adjacent said means for detecting to receive radiation from a source;
    a source of radiation;
    a head for receiving said source of radiation, said head comprising,
        a shield constructed of non-radioactive high atomic number material,
        said shield defining an opening therethrough for passage of radiation from said source, said opening being defined by a conical surface diametrically diverging away from said opening; and
        a plug disposed between said opening and said sample for precluding radiation from said source directly striking said detector.

2. An x-ray fluorescence instrument as defined in claim 1 wherein said shield is constructed of tungsten material.

3. An x-ray fluorescence instrument as defined in claim 1 wherein said plug is constructed of tungsten material.

4. An x-ray fluorescence instrument as defined in claim 3 wherein said plug includes a conical exterior surface.

5. An x-ray fluorescence instrument as defined in claim 3 wherein said plug is of a sufficient thickness to absorb radiation emanating from said source.

6. An x-ray fluorescence instrument as defined in claim 1 wherein said means for positioning a sample includes a baffle through which ambient air is passed.

7. An x-ray fluorescence instrument for detecting x-rays emanating from a sample to be measured comprising:
    a scintillation detector;
    means for positioning a sample containing particles of lead adjacent said scintillation detector;
    a source of gamma rays;
    a head for receiving said source of gamma rays, said head comprising, a shield constructed of tungsten material which substantially surrounds said source, said shield defining an opening therethrough adjacent said source for the passage of gamma rays therethrough, and an outwardly diverging conical surface disposed adjacent said opening for guiding gamma rays emanating from said source towards said sample; and
    a plug constructed of tungsten material disposed between said opening and said sample to prevent gamma rays from said source directly striking said scintillation detector.

8. An x-ray fluorescence instrument as defined in claim 7 wherein said means for positioning a sample is a filter media through which the ambient has passed.

9. An x-ray fluorescence instrument as defined in claim 8 wherein said source is Cobalt-57.

10. An x-ray fluorescence instrument as defined in claim 9 wherein said plug defines a conical exterior surface directed toward said source.

11. An x-ray fluorescence instrument as defined in claim 10 wherein said plug is approximately one to two centimeters in thickness.

* * * * *